United States Patent [19]

Kondur

[11] Patent Number: 4,580,556
[45] Date of Patent: Apr. 8, 1986

[54] ADAPTOR FOR ENDOTRACHEAL INTUBATION

[76] Inventor: Prabhakar R. Kondur, 505 Courthouse Lane, Augusta, Ga. 30901

[21] Appl. No.: 599,926

[22] Filed: Apr. 13, 1984

[51] Int. Cl.⁴ .......................................... A61M 16/00
[52] U.S. Cl. .................... 128/206.28; 128/4; 128/6; 128/912; 128/206.29
[58] Field of Search .......... 128/202.28, 203.29, 128/207.14, 207.15, 206.29, 206.28, 912, 200.26, 4, 6, 10, 11, 15, 16; 604/256, 176

[56] References Cited

U.S. PATENT DOCUMENTS

| | | | |
|---|---|---|---|
| 2,625,155 | 1/1953 | Engelder | 128/207.11 |
| 3,388,705 | 6/1968 | Grosshandler | 128/207.14 |
| 3,776,222 | 12/1973 | Smiddy | 128/6 |
| 4,233,982 | 11/1980 | Bauer et al. | 604/256 |
| 4,240,417 | 12/1980 | Holever | 128/207.15 |
| 4,351,328 | 9/1982 | Bodai | 128/207.15 |
| 4,416,273 | 11/1983 | Grimes | 128/912 |
| 4,446,864 | 5/1984 | Watson et al. | 128/207.14 |
| 4,475,548 | 10/1984 | Muto | 128/207.14 |
| 4,488,548 | 12/1984 | Agdanowski | 128/207.15 |
| 4,506,665 | 3/1985 | Andrews et al. | 128/205.25 |

FOREIGN PATENT DOCUMENTS

| | | | |
|---|---|---|---|
| 810517 | 3/1959 | United Kingdom | 128/207.14 |
| 2069849 | 9/1981 | United Kingdom | 128/204.25 |

Primary Examiner—Henry J. Recla
Attorney, Agent, or Firm—Harvey B. Jacobson; Clarence A. O'Brien

[57] ABSTRACT

An adaptor is disclosed for use with an anesthesia mask to allow an endotracheal tube and a fiberoptic laryngoscope to be passed through the mask while a patient is being ventilated under general anesthesia. The adaptor comprises a T-shaped member, one limb of which is connected to conventional anesthesia equipment and the other limb of which has a soft, flexible cover with a central opening through which the endotracheal tube and fiberoptic laryngoscope are passed. The flexibility of the cover allows endotracheal tubes of different diameter to be accommodated in the opening, and when the mask is not being used for intubation, the opening in the cover may be obturated by a plug. The adaptor may also include a further plug having a throughbore for insertion in the free end of the endotracheal tube to seal around the laryngoscope.

11 Claims, 3 Drawing Figures

ADAPTOR FOR ENDOTRACHEAL INTUBATION

BACKGROUND OF THE INVENTION

This invention relates to an adaptor for use with an anesthesia mask to enable endotracheal intubation procedures to be performed on a patient while the patient is being ventilated under general anesthesia.

While endotracheal intubation using a fiberoptic laryngoscope is a relatively simple process when a patient is "awake" and has had topical anesthesia to the upper air way, the process is complicated, inter alia by the presence of an anesthesia mask and associated equipment, when a patient is being ventilated under general anesthesia. Devices have been proposed for enabling intubation equipment to be used during general anesthesia, such equipment, at least that known to applicant, is not entirely satisfactory.

For example, applicant is aware of a device referred to as a "Patil-Syracuse Mask" marketed by Bay Medical Inc., P.O. Box 20026, St. Petersburg, Fla. 33742, and devices such as the "Trach Swivel Adaptor" and "Fiberoptic Bronchoscope Adaptor" marketed by Portex, Inc., 42 Industrial Way, Wilmington, Mass. 01887. The Swivel Adaptor which is designed for post-intubation Fiberoptic Bronchoscopy will not fit standard anesthesia masks, will not accommodate an endotracheal tube larger than 5.5 mm in diameter, will be impractical for ventilating the patient when fiberoptic laryngoscope is inside the endotrachael tube and the Patil-Syracuse Mask is expensive and unsuitable for post-intubation Fiberoptic Bronchoscopy. Further, a single mask is unsuitable for patients of all sizes, so that a range of masks in different sizes must be available.

In contrast to the known equipment, the present invention provides a simple and inexpensive adaptor suitable for use with a conventional anesthesia mask to enable a variety of intubation procedures to be carried out during general anesthesia.

STATEMENT OF PRIOR ART

The following U.S. patents relate to tracheal tube adaptors and like apparatus. However, none of these discloses apparatus for the same purpose as that of the present invention, namely for use in general anesthesia in conjunction with an anesthesia mask.

U.S. Pat. No. 2,039,142, W. F. Brehm, Apr. 28, 1936
U.S. Pat. No. 3,683,931, K. M. Chelucci, Aug. 15, 1972
U.S. Pat. No. 3,721,233 W. W. Montgomery, Mar. 20, 1973
U.S. Pat. No. 4,152,017, H. J. Abramson, May 1, 1979
U.S. Pat. No. 4,240,417, B. K. Holever, Dec. 23, 1980

SUMMARY OF THE INVENTION

The invention provides an adaptor for fitment into a cuff-like opening in an anesthesia mask, to allow passage through the mask of an endotracheal tube and fiberoptic laryngoscope while still providing supply to the mask of the oxygen or conventional gases and the like used for ventilating a patient under general anesthesia. Accordingly, the adaptor comprises, at least in a preferred form of the invention, a generally T-shaped tubular member, which may be molded in a hard plastic of the type commonly used in surgical fittings, the T-shaped member having an elongate main body portion (the crossbar of the T) for receipt of one end thereof in the mask opening, a branch (the stem of the T) extending from the body portion for connection to tubing supplying the anesthesia gases, a cover means for the other end of the main body portion having an opening therethrough for receipt of the endotrachael tube and means for obturating the opening when the endotracheal tube (and associated laryngoscope) is not in use.

The cover means for the other end of the main body portion of the T-shaped member may, for example, comprise a thin flexible diaphragm-type cover, e.g. of a soft plastic material such as silastic having a skirt portion adapted to stretch over a lip of said other end of main body portion, and a cover portion with a central opening for receiving an endotracheal tube. The stretchable nature of the cover allows endotracheal tubes of different diameter to be inserted through the opening. The means for obturating the opening in the cover may comprise a plug of hard rubber or the like.

In one preferred form of the invention, the cover and plug may be secured by suitable cords to a ring fitting integrally molded on the T-shaped member for convenient and ready access. Further, the adaptor may include a second plug on a longer thread attached to the fitting for insertion over the end of the endotracheal tube, the further plug having a central throughbore for receiving the laryngoscope extending through the endotracheal tube.

These together with other objects and advantages which will become subsequently apparent reside in the details of construction and operation as more fully hereinafter described and claimed, reference being had to the accompanying drawings forming a part hereof, wherein like numerals refer to like parts throughout.

DESCRIPTION OF PREFERRED EMBODIMENT

Figure 1:
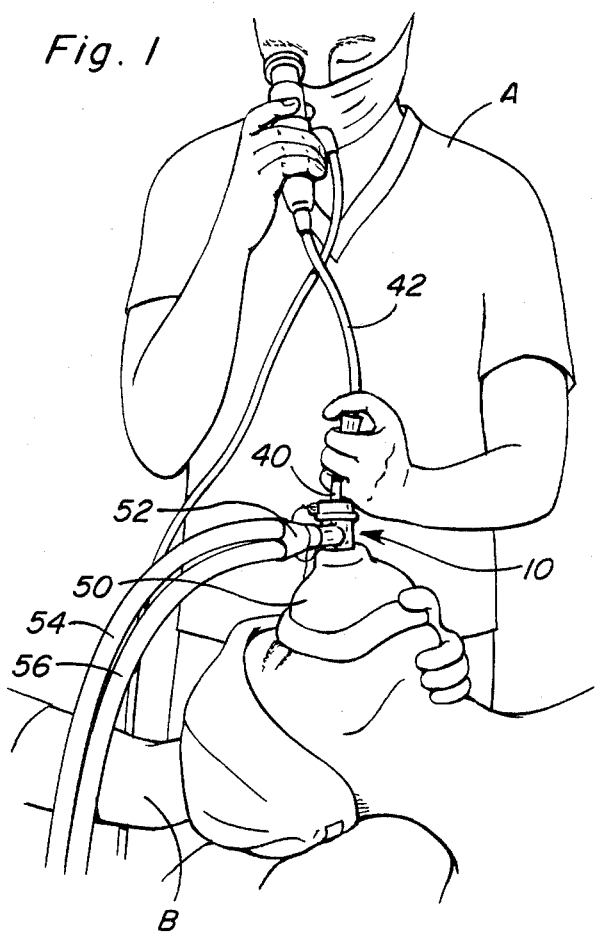
FIG. 1 is a perspective view of a patient under general anesthesia in the course of fiberoptic endotracheal intubation using an anesthesia mask equipped with an adaptor in accordance with the invention.
Figure 2:
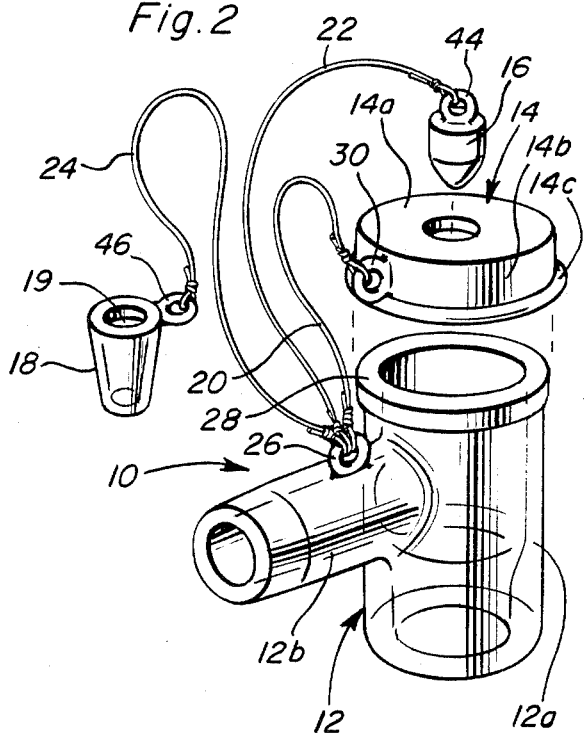
FIG. 2 is an enlarged perspective view of the adaptor.

Referring initially to FIG. 2, there is illustrated an endotracheal intubation adaptor 10 in accordance with the invention, comprising a T-shaped member 12, a cover 14, first and second plugs 16, 18 and cords 20, 22, 24 securing the cover and plugs to a ring 26 on the T-shaped member.

Member 12 is molded in a hard, preferably transparent plastic of a type well known in surgical applicances, and includes an elongate main body portion 12a open at each end, and a branch 12b opening into the main body portion. The length of portion 12a may be about 40 mm, its outer diameter about 22 mm, inner diameter at the top about 18 mm, and inner diameter at the bottom about 15 mm, with the junction between the different diameter portions comprising a smooth curve situated about 10 mm from the lower end of the body portion. The upper open end of portion 12a is formed with a projecting annular rim or lip 28 of about 2 mm×2 mm.

Branch 12b may have an outer diameter of about 15 mm, tapering at its distal end to about 14.5 mm, the branch centerline being about 25 mm from the lower end of portion 12a and the branch having a length of about 20 mm. Ring 26 may be integrally molded on the outer surface of branch 12b.

Cover 14 is made of a soft resiliently stretchable plastic such as silastic of diaphragm-like thickness and having a cover portion 14a and a skirt portion 14b terminating in a rim 14c.

The diameter of the cover may be about 22 mm, so that it may stretch and snap over lip 28 of member 12. An opening 32 of about 5 mm may be formed in the cover portion, the resilience of the cover allowing the opening to stretch and accommodate endotracheal tubes of up to about 10 mm in diameter. A ring 30 is provided on the cover to attach cord 20.

Figure 3:
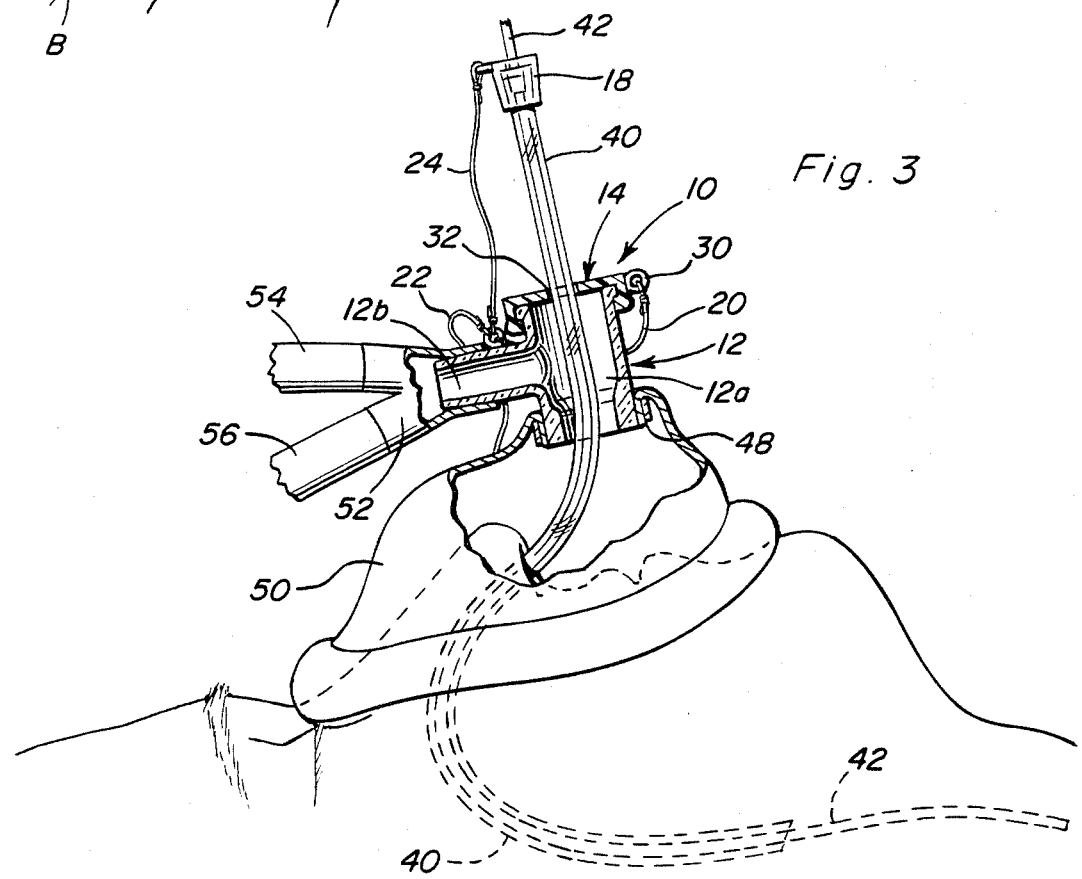
FIG. 3 is an enlarged view similar to FIG. 1, part broken away and showing the relationship of the invention components during intubation with the endotracheal tube and laryngoscope extending into the patient's trachia.

The first plug 16 may be of a hard plastic material of about 7 mm in diameter so as to fit tightly into opening 32 to obturate the opening when required. Second plug 18 may be of a softer plastic material and be of frusto-conical shape, the upper end being about 12 mm in diameter, the lower end about 5 mm diameter and the length about 10 mm. Plug 18 has a central throughbore 19 of about 4 mm diameter, the plug being flexible enough to receive a laryngoscope therethrough of about 6 mm diameter. In use, plug 18 may be fitted over the upper end of an endotracheal tube 40 (see FIG. 3) to form a seal around laryngoscope 42. Plugs 16 and 18 have cord attachment rings 44, 46, respectively.

For use of the adaptor, the lower end of T-member 12 may be secured in standard cuff opening 48 of a conventional anesthesia mask 50, and branch 12b connected through a Y-fitting 52 to conventional anesthesia supply lines 54, 56, for example, of circle system anesthesia equipment to ventilate a patient under general anesthesia. During anesthesia, the upper end of member 12 may be covered and sealed by cover 14 and plug 16 when there is no requirement for tracheal intubation. When tracheal intubation is required however, endotracheal tube 40 of suitable diameter (up to about 10 mm) may be inserted through opening 32 of cover 14 in place of plug 16, with laryngoscope 42 inserted through the tube and with plug 18 sealing the junction between the tube and scope. Generally, a first operator A will perform the intubation, while a second operator B administers the anesthesia.

As previously noted, the nature of cover 14 and plug 18 allows endotracheal tubes and laryngoscopes of varying size to be accommodated, and the adapter 10 provides a simple and convenient means enabling endotracheal intubations to be performed during general anesthesia using conventional anesthesia equipment. In a modification of the invention, cover 14 may be permanently attached to the top of the T-shaped member.

While the apparatus has been described and illustrated in use for nasal laryngoscopy, it may also be used in a similar manner for oral laryngoscropy and for post-intubation bronchoscopy.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. An adaptor for use with an anesthesia mask to allow passage through the mask of an endotracheal tube and laryngoscope or the like while providing supply to the mask of gases used in ventilating a patient such as in general anesthesia, the adaptor comprising a generally T-shaped tubular member having an elongate open-ended main body portion for receipt at one end thereof in a cuff-like opening or the like of an anesthesia mask, a branch extending from the main body portion for connection to tubing supplying anesthesia or like gases, a cover means for the other end of the main body portion having an opening therethrough for receipt of an endotracheal tube, and means for obturating the opening when the endotracheal tube and associated equipment is not in use, wherein the cover means comprises a thin flexible diaphragm-like cover having a skirt portion adapted to stretch over said other end of said main body portion, and a cover portion formed with said opening, wherein the means for obturating said opening comprises a solid plug secured by a cord to said T-shaped member along with a further cord securing the cover to the T-shaped member, the adaptor including a further plug secured by a cord to the T-shaped member, the further plug being adapted for receipt over the open end of an endotracheal tube and having a throughbore formed therein for passage of a laryngoscope through the plug.

2. The invention of claim 1 wherein said opening is about 5 mm in nominal diameter and is adapted to accommodate endotracheal tubes up to about 10 mm in diameter when the cover is stretched.

3. The invention of claim 1 wherein said other end of said main body portion is formed with an external annular lip over which the cover stretches.

4. The invention of claim 1 wherein the further plug is formed of a soft plastic material in a frusto-conical shape.

5. The invention of claim 1 wherein the T-shaped member is molded in a hard plastic material.

6. The invention of claim 5 wherein the material is transparent.

7. In combination with an anesthesia mask having an opening therethrough, a fitting for accommodating an endotracheal tube and associated laryngoscope extending through said opening in the mask for performing endotracheal intubation during general anesthesia, the fitting comprising an open ended tube extending outwardly from the opening in the mask, the tube having an open end covered by a flexible diaphragm-type cover, an opening substantially centrally disposed in the cover for receiving an endotracheal tube therethrough, obturating means for the opening when the tube is not in use, and a branch tube extending from the open-ended tube for supplying anesthesia gases to the mask, wherein the obturating means comprises a solid plug secured by a cord to said fitting for plugging said opening and the combination includes a further plug secured by a cord to said fitting for insertion over the exposed end of the endotracheal tube, the further plug having a throughbore for passage of a laryngoscope.

8. The invention of claim 7 wherein the cover is stretched over the open end of the tube and is removable from the open end of the tube.

9. The invention of claim 7 wherein the opening in the cover is about 5 mm in nominal diameter and can receive endotracheal tubes up to about 10 mm in diameter when the cover is stretched.

10. The invention of claim 7 wherein the cover is removably mounted on the open end of the tube, the cover and both said plugs being secured to a common mounting means on one of said open ended tube and branch tube by means of separate cords.

11. An adaptor for use with an anesthesia mask to allow passage through the mask of an endotracheal tube and laryngoscope or the like while providing supply to the mask of gases used in ventilating a patient such as in general anesthesia, the adaptor comprising a generally T-shaped tubular member having an elongate open-ended main body portion for receipt at one end thereof in a cuff-like opening or the like of an anesthesia mask, a branch extending from the main body portion for connection to tubing supplying anesthesia or like gases, a cover means for the other end of the main body portion having an opening therethrough for receipt of an endotracheal tube, and means for obturating the opening when the endotracheal tube and associated equipment is not in use, wherein the means for obturating said opening comprises a solid plug secured by a cord to said T-shaped member and a further plug secured by a cord to the T-shaped member, the further plug being adapted for receipt over the open end of an endotracheal tube and having a throughbore formed therein for passage of a laryngoscope through the plug.

* * * * *